US010796805B2

(12) United States Patent
Lotan et al.

(10) Patent No.: US 10,796,805 B2
(45) Date of Patent: Oct. 6, 2020

(54) ASSESSMENT OF A PULMONARY CONDITION BY SPEECH ANALYSIS

(71) Applicant: CORDIO MEDICAL LTD., Or-Yehuda (IL)

(72) Inventors: Chaim Lotan, Jerusalem (IL); Sigal Kremer-Tal, Ramat Hasharon (IL); Aviv Lotan, Tel Aviv (IL); Zeev Schlik, Ramat Gan (IL); Avinoam Gemer, Kiryat Ono (IL); Yehuda Snir, Kiryat Tivon (IL); Yonatan Sasson, Tel Aviv (IL); Margarita Sheinkerman, Tel Aviv (IL)

(73) Assignee: CORDIO MEDICAL LTD., Or-Yehuda (IL)

( * ) Notice: Subject to any disclaimer, the term of this patent is extended or adjusted under 35 U.S.C. 154(b) by 0 days.

(21) Appl. No.: 15/759,525

(22) PCT Filed: Oct. 5, 2016

(86) PCT No.: PCT/IB2016/055954
§ 371 (c)(1),
(2) Date: Mar. 13, 2018

(87) PCT Pub. No.: WO2017/060828
PCT Pub. Date: Apr. 13, 2017

(65) Prior Publication Data
US 2019/0080803 A1 Mar. 14, 2019

Related U.S. Application Data

(60) Provisional application No. 62/238,732, filed on Oct. 8, 2015.

(51) Int. Cl.
*G16H 80/00* (2018.01)
*G10L 25/24* (2013.01)
(Continued)

(52) U.S. Cl.
CPC ............... *G16H 80/00* (2018.01); *A61B 5/08* (2013.01); *A61B 5/4803* (2013.01);
(Continued)

(58) Field of Classification Search
CPC ........ G16H 80/00; G16H 50/30; G10L 25/18; G10L 15/1822; G10L 25/66; G10L 25/15;
(Continued)

(56) References Cited

U.S. PATENT DOCUMENTS 4,838,275 A    6/1989 Lee
5,853,005 A    12/1998 Scanlon
(Continued)

FOREIGN PATENT DOCUMENTS

CN    102125427 A    7/2011
CN    102423262 A    4/2012
(Continued)

OTHER PUBLICATIONS

U.S. Appl. No. 14/426,301 office action dated Oct. 19, 2018.
(Continued)

*Primary Examiner* — Bharatkumar S Shah
(74) *Attorney, Agent, or Firm* — Kligler & Associates Patent Attorneys Ltd (57) ABSTRACT

Described embodiments include apparatus that includes a network interface (28) and a processor (30). The processor is configured to receive, via the network interface, speech of a subject (22) who suffers from a pulmonary condition related to accumulation of excess fluid, to identify, by analyzing the speech, one or more speech-related parameters of the speech, to assess, in response to the speech-related parameters, a status of the pulmonary condition, and to generate, in response thereto, an output indicative of the status of the pulmonary condition. Other embodiments are also described.

39 Claims, 3 Drawing Sheets

(51) Int. Cl.
  *G10L 25/15* (2013.01)
  *G10L 25/66* (2013.01)
  *A61B 5/00* (2006.01)
  *A61B 5/08* (2006.01)
  *G16H 50/30* (2018.01)
  *G16B 40/00* (2019.01)
  *G10L 15/18* (2013.01)
  *G10L 25/18* (2013.01)

(52) U.S. Cl.
  CPC .......... *A61B 5/4878* (2013.01); *A61B 5/6898* (2013.01); *A61B 5/7257* (2013.01); *G10L 15/1822* (2013.01); *G10L 25/15* (2013.01); *G10L 25/18* (2013.01); *G10L 25/24* (2013.01); *G10L 25/66* (2013.01); *G16B 40/00* (2019.02); *G16H 50/30* (2018.01)

(58) Field of Classification Search
  CPC ....... G10L 25/24; G16B 40/00; A61B 5/4878; A61B 5/4803; A61B 5/08; A61B 5/6898; A61B 5/7257
  USPC .......................................................... 704/225
  See application file for complete search history.

(56) References Cited

U.S. PATENT DOCUMENTS

| | | | |
|---|---|---|---|
| 5,864,810 A | 1/1999 | Digalakis et al. | |
| 6,168,568 B1 | 1/2001 | Gavriely | |
| 6,241,683 B1 | 6/2001 | Macklem et al. | |
| 6,289,313 B1 | 9/2001 | Heinonen et al. | |
| 6,389,393 B1 | 5/2002 | Gong | |
| 6,396,416 B1 | 5/2002 | Kuusela et al. | |
| 6,600,949 B1 | 7/2003 | Turcott | |
| 7,092,874 B2 | 8/2006 | Clavbo | |
| 7,225,013 B2 | 5/2007 | Geva et al. | |
| 7,226,422 B2 | 6/2007 | HatlestSad et al. | |
| 7,267,652 B2 | 9/2007 | Coyle et al. | |
| 7,283,962 B2 | 10/2007 | Meyerhoff et al. | |
| 7,363,226 B2 | 4/2008 | Shiomi et al. | |
| 7,398,213 B1 | 7/2008 | Levanon et al. | |
| 7,457,753 B2 | 11/2008 | Moran et al. | |
| 7,529,670 B1 | 5/2009 | Michaelis | |
| 7,762,264 B1 | 7/2010 | Raming et al. | |
| 8,591,430 B2 | 11/2013 | Amurthur et al. | |
| 8,684,900 B2 | 4/2014 | Tran | |
| 8,689,606 B2 | 4/2014 | Schellekens et al. | |
| 8,784,311 B2 | 7/2014 | Shrivastav et al. | |
| 9,070,357 B1 | 6/2015 | Kennedy et al. | |
| 9,138,167 B1 | 9/2015 | Leydon | |
| 9,445,763 B2 | 9/2016 | Davis et al. | |
| 9,492,096 B2 | 11/2016 | Brockway et al. | |
| 9,579,056 B2 | 2/2017 | Rosenbek et al. | |
| 9,685,174 B2 | 6/2017 | Karam et al. | |
| 9,922,641 B1 | 3/2018 | Chun | |
| 2002/0059029 A1 | 5/2002 | Todder et al. | |
| 2003/0115054 A1* | 6/2003 | Iso-Sipila ................ G10L 15/02 704/233 |
| 2003/0220790 A1 | 11/2003 | Kepuska | |
| 2006/0058697 A1 | 3/2006 | Mochizuki et al. | |
| 2006/0116878 A1 | 6/2006 | Nagamine | |
| 2006/0167385 A1 | 7/2006 | Guion | |
| 2006/0293609 A1 | 12/2006 | Stahmann et al. | |
| 2007/0005357 A1 | 1/2007 | Moran et al. | |
| 2007/0225975 A1 | 9/2007 | Imoto | |
| 2008/0013747 A1 | 1/2008 | Tran | |
| 2008/0275349 A1 | 11/2008 | Halperin et al. | |
| 2009/0036777 A1* | 2/2009 | Zhang .................. A61B 5/4878 600/459 |
| 2009/0099848 A1 | 4/2009 | Lerner et al. | |
| 2009/0326937 A1 | 12/2009 | Chitsaz et al. | |
| 2010/0201807 A1 | 8/2010 | McPherson | |
| 2011/0021940 A1 | 1/2011 | Chu et al. | |
| 2011/0092779 A1 | 4/2011 | Chang et al. | |
| 2011/0125044 A1 | 5/2011 | Rhee | |
| 2011/0184250 A1 | 7/2011 | Schmidt et al. | |
| 2012/0041279 A1 | 2/2012 | Freeman et al. | |
| 2012/0116186 A1 | 5/2012 | Shrivastav et al. | |
| 2012/0283598 A1 | 8/2012 | Horii et al. | |
| 2012/0265024 A1 | 10/2012 | Shrivastav et al. | |
| 2013/0018274 A1 | 1/2013 | O'Neill | |
| 2013/0158434 A1 | 6/2013 | Shen et al. | |
| 2014/0005564 A1 | 1/2014 | Ivanovic et al. | |
| 2014/0073993 A1 | 3/2014 | Poellalbauer et al. | |
| 2014/0153794 A1 | 6/2014 | Varaklis et al. | |
| 2014/0249424 A1 | 9/2014 | Fan et al. | |
| 2014/0302472 A1 | 10/2014 | Fletcher | |
| 2014/0314212 A1 | 10/2014 | Bentley et al. | |
| 2015/0073306 A1* | 3/2015 | Abeyratne .......... G06K 9/00523 600/586 |
| 2015/0126888 A1 | 5/2015 | Patel et al. | |
| 2015/0127350 A1* | 5/2015 | Agiomyrgiannakis ...................... G10L 13/02 704/266 |
| 2015/0216448 A1 | 8/2015 | Lotan et al. | |
| 2015/0265205 A1 | 9/2015 | Rosenbek et al. | |
| 2016/0015289 A1 | 1/2016 | Simon et al. | |
| 2016/0045161 A1 | 2/2016 | Alshaer et al. | |
| 2016/0081611 A1* | 3/2016 | Hampton ............... G16H 40/67 600/538 |
| 2016/0095545 A1 | 4/2016 | Levanon | |
| 2016/0302003 A1* | 10/2016 | Rahman .................. H04R 1/46 |
| 2017/0069312 A1 | 3/2017 | Sundararajan et al. | |
| 2017/0084295 A1 | 3/2017 | Tsiartas et al. | |
| 2017/0280239 A1 | 9/2017 | Sekiya et al. | |
| 2018/0108440 A1* | 4/2018 | Stevens ................ G06N 3/0445 |
| 2018/0125444 A1 | 5/2018 | Kahlman et al. | |
| 2018/0296092 A1 | 10/2018 | Hassan et al. | |

FOREIGN PATENT DOCUMENTS

| | | |
|---|---|---|
| CN | 202261466 U | 5/2012 |
| CN | 102497472 A | 6/2012 |
| CN | 107622797 A | 1/2018 |
| EP | 1855594 A1 | 11/2007 |
| EP | 2124223 A1 | 11/2009 |
| EP | 2438863 A1 | 4/2012 |
| GB | 1219618 A | 1/1971 |
| GB | 2493458 A | 2/2013 |
| JP | 04082538 A | 3/1992 |
| JP | 09173320 A | 7/1997 |
| WO | 2006079062 A1 | 7/2006 |
| WO | 2010015865 A1 | 2/2010 |
| WO | 2010123483 A2 | 10/2010 |
| WO | 2012038903 A2 | 3/2012 |
| WO | 2012104743 A2 | 8/2012 |
| WO | 2013043847 A1 | 3/2013 |
| WO | 2013170131 A1 | 11/2013 |
| WO | 2014037843 A1 | 3/2014 |
| WO | 2014045257 A1 | 3/2014 |
| WO | 2014188408 A1 | 11/2014 |
| WO | 2016028495 A1 | 2/2016 |
| WO | 2017060828 A1 | 4/2017 |
| WO | 2017068582 A1 | 7/2017 |
| WO | 2018021920 A1 | 2/2018 |

OTHER PUBLICATIONS

Wang et al., "Accuracy of perceptual and acoustic methods for the detection of inspiratory loci in spontaneous speech", Behavior Research Methods, vol. 44, Issue 4, pp. 1121-1128, Dec. 2012.

Gillespie et al., "The Effects of Hyper- and Hypocapnia on Phonatory Laryngeal Airway Resistance in Women", Research Article, Journal of Speech, Language, and 638 Hearing Research, vol. 58, pp. 638-652, Jun. 2015.

Murton et al., "Acoustic speech analysis of patients with decompensated heart failure: A pilot study", The Journal of the Acoustical Society of America, vol. 142, Issue 4, pp. 1-28, Oct. 24, 2017.

Hickey., "App lets you monitor lung health using only a smartphone", 5 pages, Sep. 18, 2012.

(56) References Cited

OTHER PUBLICATIONS

Gandler et al., "Mobile FEV: Evaluation of iPhone Spirometer", 1 page, Feb. 14, 2013.
Abushakra et al., "Lung capacity estimation through acoustic signal of breath", 13th IEEE International Conference on BioInformatics and BioEngineering, pp. 386-391, Nov. 11-Nov. 13, 2012.
G.P. Imports, Inc., "Spirometer Pro", 3 pages, Jan. 8, 2010.
Larson et al., "SpiroSmart: using a microphone to measure lung function on a mobile phone", Proceedings of the 2012 ACM Conference on Ubiquitous Computing (UbiComp '12), pp. 280-289, Sep. 5-8, 2012.
Abushakra et al., "An Automated Approach Towards Estimating Lung Capacity from Respiration Sounds", IEEE Healthcare Innovations Conference (HIC'12), 5 pages, Jan. 2012.
Williammson et al., "Vocal and Facial Biomarkers of Depression Based on Motor Incoordination and Timing", 4th International Audio/Visual Emotion Challenge and Workshop: Depression Challenge, Orlando, Florida, USA , 8 pages Nov. 7, 2014.
Ciccarelli et al., "Neurophysiological Vocal Source Modeling for Biomarkers of Disease", INTERSPEECH 2016: Understanding Speech Processing in Humans and Machines, Technical Program, San Francisco, USA, 7 pages, Sep. 8-12, 2016.
Helfer et al., "Classification of depression state based on articulatory precision", Proceedings of the 14th Annual Conference of the International Speech Communication Association (INTERSPEECH), pp. 2172-2176, year 2013.
Horwitz., "Vocal Modulation Features in the Prediction of Major Depressive Disorder Severity", 115 pages, Master Thesis, Massachusetts Institute of Technology, Sep. 2014.
Hillel., "Using phonation time to estimate vital capacity in amyotrophic lateral sclerosis", Arch Phys Med Rehabil, vol. 70, pp. 618-620, Aug. 1989.
Yanagihara., "Phonation and Respiration", Folia Phoniat, vol. 18, pp. 323-340, 1966.
Dewar et al., "Chronic obstructive pulmonary disease: diagnostic considerations.", American Academy of Family Physicians, vol. 73, pp. 669-676, Feb. 2006.
Solomon et al., "Respiratory and laryngeal contributions to maximum phonation duration", Journal of voice, vol. 14, No. 3, pp. 331-340, Sep. 2000.
Dogan et al., "Subjective and objective evaluation of voice quality in patients with asthma", Journal of voice, vol. 21, No. 2, pp. 224-230, Mar. 2007.
Orenstein et al.,"Measuring ease of breathing in young patients with cystic fibrosis", Pediatric Pulmonology, vol. 34, No. 6, pp. 473-477, Aug. 8, 2002.
U.S. Appl. No. 14/426,301 office action dated Apr. 5, 2018.
Lee et al., "Speech Segment Durations Produced by Healthy and Asthmatic Subjects", Journal of Speech and Hearing Disorders, vol. 653, pp. 186-193, May 31, 1988.
EP Application # 16853171.3 Extended Search Report dated Apr. 23, 2019.
International Application # PCT/IB2019/058408 search report dated Dec. 31, 2019.
Mulligan et al., "Detecting regional lung properties using audio transfer functions of the respiratory system", 31st Annual International Conference of the IEEE EMBS, pp. 5697-5700, Sep. 2-6, 2009.
EP Application # 13834998.0 office action dated Feb. 5, 2020.
Lee et al., "Consistency of acoustic and aerodynamic measures of voice production over 28 days under various testing conditions", Journal of Voice, vol. 13, issue 4, pp. 477-483, Dec. 1, 1999.
Walia et al., "Level of Asthma: A Numerical Approach based on Voice Profiling", IJEDR(International Journal of Engineering Development and Research), vol. 4, issue 4, pp. 717-722, year 2016.
European Application # 19201720.0 search report dated Mar. 3, 2020.
U.S. Appl. No. 16/157,118 office action dated May 5, 2020.
International Application # PCT/IB2020/051016 search report dated May 21, 2020.
International Application # PCT/IB2020/051018 search report dated Jun. 2, 2020.
European Application # 20158058.6 search report dated Jul. 23, 2020.
European Application # 20158069.3 search report dated Jul. 24, 2020.
Japanese Application # 2018-516182 office action action dated Jul. 15, 2020.
Christina et al., "HMM-based speech recognition system for the dysarthric speech evaluation of articulatory subsystem", International Conference on Recent Trends in Information Technology, pp. 54-59, Apr. 1, 2012.
Wang et al., "Vocal folds disorder detection using pattern recognition methods", 29th Annual International conference of the IEEE Engineering in Medicine and Biology Society, pp. 3253- 3256, Aug. 22-26, 2007.
Rabiner., "A Tutorial on Hidden Markov Models and Selected Applications in Speech Recognition", Proceedings of the IEEE, vol. 77, issue 2, pp. 257-286, Feb. 1989.
Masada et al., "Feature Extraction by ICA and Clustering for Lung Sound Classification", IPSJ Symposium Series, vol. 2007, pp. 1-9, year 2007.

* cited by examiner

ASSESSMENT OF A PULMONARY CONDITION BY SPEECH ANALYSIS

CROSS-REFERENCE TO RELATED APPLICATIONS

The present application claims the benefit of U.S. Provisional Application No. 62/238,732, entitled "Assessment of a pulmonary condition using voice analysis," filed Oct. 8, 2015, whose disclosure is incorporated herein by reference.

FIELD OF THE INVENTION

Embodiments of the present invention relate to the diagnosis and treatment of medical conditions, particularly pulmonary conditions.

BACKGROUND

Pulmonary edema is an accumulation of fluid within the parenchyma and air spaces of the lungs. It leads to impaired gas exchange and may cause respiratory failure.

Pleural effusion is excess fluid that accumulates in the pleural cavity, the fluid-filled space that surrounds the lungs. This excess fluid can impair breathing by limiting the expansion of the lungs.

US Patent Application Publication 2015/0073306, whose disclosure is incorporated herein by reference, describes a method of operating a computational device to process patient sounds, the method comprising the steps of: extracting features from segments of said patient sounds; and classifying the segments as cough or non-cough sounds based upon the extracted features and predetermined criteria; and presenting a diagnosis of a disease related state on a display under control of the computational device based on segments of the patient sounds classified as cough sounds.

U.S. Pat. No. 7,267,652, whose disclosure is incorporated herein by reference, describes systems and methods for processing respiratory signals derived generally from respiratory plethysmography, and especially from respiratory inductive plethysmographic sensors mounted on a garment for ambulatory recording. The systems and methods provide signal filtering for artifact rejection, and calibration of sensor data to produce outputs indicative of lung volumes. This reference also describes systems and methods directed to processing lung volume signals, however measured or derived, to provide determination of respiratory parameters and recognition of selected respiratory events.

US Patent Application Publication 2011/0184250, whose disclosure is incorporated herein by reference, describes a computer-implemented method and system for assisting a plurality of patients manage chronic health conditions. The method, for each patient, comprises: (a) receiving information from the patient or a member of a patient care network on an expected patient activity at a given future time period; (b) determining expected transient local ambient conditions in the patient's surroundings during the expected patient activity at the given future time period; (c) predicting health exacerbations for the patient using a stored computer model of the patient based on a desired patient control set-point range, the expected patient activity, and the expected transient local ambient conditions; and (d) proactively sending a message to the patient or a member of the patient care network before the given future time period, the message alerting the patient or a member of the patient care network of the predicted health exacerbations for the patient and identifying one or more corrective actions for the patient to avoid or mitigate the predicted health exacerbations.

PCT Publication WO 2014/037843, whose disclosure is incorporated herein by reference, describes a computerized method and system for measuring a user's lung capacity and stamina, to detect Chronic Heart Failure, COPD or Asthma, comprising: providing a client application on a user's mobile communication device, said client application comprising executable computer code for: instructing the user to fill his lungs with air and utter vocal sounds within a certain range of loudness (decibels) while exhaling; receiving and registering by the mobile communication device said user's vocal sounds; stopping the registering of vocal sounds; measuring the length of the vocal sounds receiving time within said range of loudness, said time proportionate the user's lung volumes; and displaying the length of sound received time results on the mobile communication device screen.

SUMMARY OF THE INVENTION

There is provided, in accordance with some embodiments of the present invention, apparatus that includes a network interface and a processor. The processor is configured to receive, via the network interface, speech of a subject who suffers from a pulmonary condition related to accumulation of excess fluid, to identify, by analyzing the speech, one or more speech-related parameters of the speech, to assess, in response to the speech-related parameters, a status of the pulmonary condition, and to generate, in response thereto, an output indicative of the status of the pulmonary condition.

In some embodiments, the processor is configured to analyze the speech by performing a spectral analysis of the speech.

In some embodiments, the processor is configured to analyze the speech by performing a cepstral analysis of the speech.

In some embodiments, the processor is further configured to identify, by analyzing the speech, a meaning of the speech, and the processor is configured to assess the status in response to the meaning.

In some embodiments, the processor is further configured to prompt the subject to provide, by orally responding to a question, the speech.

In some embodiments, the processor is configured to prompt the subject to provide the speech by:
placing a call to the subject, and
upon the subject answering the call, asking the question to the subject.

In some embodiments, the condition is selected from the group consisting of: pulmonary edema, and pleural effusion.

In some embodiments, the processor is configured to generate the output by providing an alert indicative of a deterioration in the status.

In some embodiments, the speech-related parameters include at least one formant frequency of the speech.

In some embodiments, the processor is configured to assess the status of the pulmonary condition by comparing the formant frequency to a baseline frequency.

In some embodiments, the processor is configured to analyze the speech by:
for each frame of a time-domain signal that represents the speech:
computing a cepstrum of the frame,
subsequently, applying a low-pass cepstral lifter to the cepstrum of the frame,
subsequently, inverse-transforming the liftered cepstrum to a frequency domain, and subsequently, identifying a formant frequency of the frame, by identifying a peak of the inverse-transformed liftered cepstrum, and identifying the formant frequency, based on the respective formant frequencies of the frames.

In some embodiments, the processor is configured to analyze the speech by:

selecting at least one portion of the speech for analysis, based on one or more metrics selected from the group consisting of: an energy level of the speech, a stability of a pitch of the speech, a confidence in a calculation of the pitch of the speech, and a stability of a formant frequency of the speech, and subsequently, analyzing the selected portion of the speech.

In some embodiments, the processor is configured to assess the status of the pulmonary condition by applying a machine-learned model to the speech-related parameters.

In some embodiments, the speech-related parameters include a set of mel-frequency cepstrum coefficients (MFCCs).

In some embodiments, the speech-related parameters include a set of derivatives of mel-frequency cepstrum coefficients (MFCCs).

In some embodiments, the speech-related parameters include a set of relative spectral transform-perceptual linear prediction (RASTA-PLP) cepstrum components.

In some embodiments, the speech-related parameters include a set of relative spectral transform-perceptual linear prediction (RASTA-PLP) spectrum components.

In some embodiments, the processor is configured to assess the status of the pulmonary condition without identifying any cough sounds, and without identifying any wheezing sounds, in the speech.

In some embodiments, the processor is configured to analyze the speech of the subject without first prompting the subject to provide the speech.

There is further provided, in accordance with some embodiments of the present invention, a method that includes, using a processor, by analyzing speech of a subject who suffers from a pulmonary condition related to accumulation of excess fluid, identifying one or more speech-related parameters of the speech. The method further includes, in response to the speech-related parameters, automatically assessing a status of the pulmonary condition, and, in response thereto, generating an output indicative of the status of the pulmonary condition.

There is further provided, in accordance with some embodiments of the present invention, a system that includes a mobile communication terminal and a server. The server includes a processor configured to receive, from the mobile communication terminal, speech of a subject who suffers from a pulmonary condition related to accumulation of excess fluid, to identify, by analyzing the speech, one or more speech-related parameters of the speech, to assess, in response to the speech-related parameters, a status of the pulmonary condition, and to generate, in response thereto, an output indicative of the status of the pulmonary condition.

There is further provided, in accordance with some embodiments of the present invention, a computer software product including a tangible non-transitory computer-readable medium in which program instructions are stored. The instructions, when read by a processor, cause the processor to receive speech of a subject who suffers from a pulmonary condition related to accumulation of excess fluid, to identify, by analyzing the speech, one or more speech-related parameters of the speech, to assess, in response to the speech-related parameters, a status of the pulmonary condition, and to generate, in response thereto, an output indicative of the status of the pulmonary condition.

There is further provided, in accordance with some embodiments of the present invention, apparatus that includes an acoustic sensor and a processor. The processor is configured to receive, via the acoustic sensor, speech of a subject who suffers from a pulmonary condition related to accumulation of excess fluid, to identify, by analyzing the speech, one or more speech-related parameters of the speech, to assess, in response to the speech-related parameters, a status of the pulmonary condition, and to generate, in response thereto, an output indicative of the status of the pulmonary condition.

The present invention will be more fully understood from the following detailed description of embodiments thereof, taken together with the drawings, in which:

DETAILED DESCRIPTION OF EMBODIMENTS

Overview

Embodiments of the present invention provide methods and systems that assess the status of a pulmonary condition, such as pulmonary edema or pleural effusion condition, that is related to accumulation of excess fluid in or near the lungs. In some embodiments, a system that assesses the status of a pulmonary condition comprises a smartphone and a remote server. The smartphone records the subject as the subject speaks, and then sends the recorded speech signal to the remote server for analysis. By automatically analyzing the signal, the remote server identifies one or more speech-related parameters of the speech, and, in response to the parameters, assesses the status of the condition. The server then generates an output to the smartphone that drives the smartphone, in turn, to generate an output, such as a visual output, that indicates the status of the condition. Alternatively or additionally, in the event of a deterioration in the subject's condition, the server may alert an emergency call center, and/or the subject's physician or caregiver, of the deterioration, as described below.

Typically, the speech-related parameters, upon which the assessment is based, include spectral and/or cepstral properties of the speech, such as at least one formant frequency of the speech. Although formant frequencies are usually associated with the vocal tract or upper airway, embodiments of the present invention capitalize on the observation that a change in a formant frequency may also indicate a change in the amount of fluid present in the parenchyma, pleural cavity, or other portion of anatomy that belongs to, or is near, the lungs. In particular, it has been observed that an increase in a formant frequency indicates an increase in the amount of fluid, and vice versa. The system may therefore identify a deterioration in the status of the condition, based on an increase in a formant frequency, and vice versa.

Alternatively or additionally, the system may assess the status of the condition, by applying a machine-learned model to particular parameters, or "features," extracted from the speech signal. Such a model may include a regressor, which outputs a number indicative of the status. For example, the regressor may output a number that indicates, relative to a baseline, an estimated amount of fluid inside, or near, the lungs. Alternatively or additionally, such a model may include a classifier, which classifies the current status of the pulmonary condition, and/or classifies the current status of the subject based on the current status of the pulmonary condition. For example, such a classifier may classify the subject as "in need of dialysis" or "not in need of dialysis."

It is emphasized that embodiments of the present invention do not necessarily require the identification of cough sounds, wheezing sounds, breathing sounds (e.g., cackles), or any other non-speech-related parameters, in order to assess the status of the pulmonary condition. Rather, the assessment may be based only on speech-related parameters, such as formant frequencies of the subject's speech, and/or any of the other speech-related parameters described herein. Moreover, the subject need not necessarily be prompted, at any particular time, to utter any particular sounds, to say any particular words, or even to speak naturally. Rather, the system may analyze spoken sentences obtained from the subject's normal, daily conversations on his smartphone. (Notwithstanding the above, in some embodiments, the subject may be prompted to utter particular sounds, and/or say particular words, particularly if the analysis of the subject's "natural" speech is inconclusive.)

In general, the embodiments described herein facilitate early detection of, and intervention with respect to, a deterioration in the subject's condition, such that hospitalization of the subject may not be necessary. For example, the embodiments described herein facilitate evaluating the effectiveness of the particular type and/or dosage of medication that the subject is taking, such that, if a deterioration is observed, the particular type and/or dosage of medication may be adjusted, before hospitalization is required.

System Description

Figure 1:
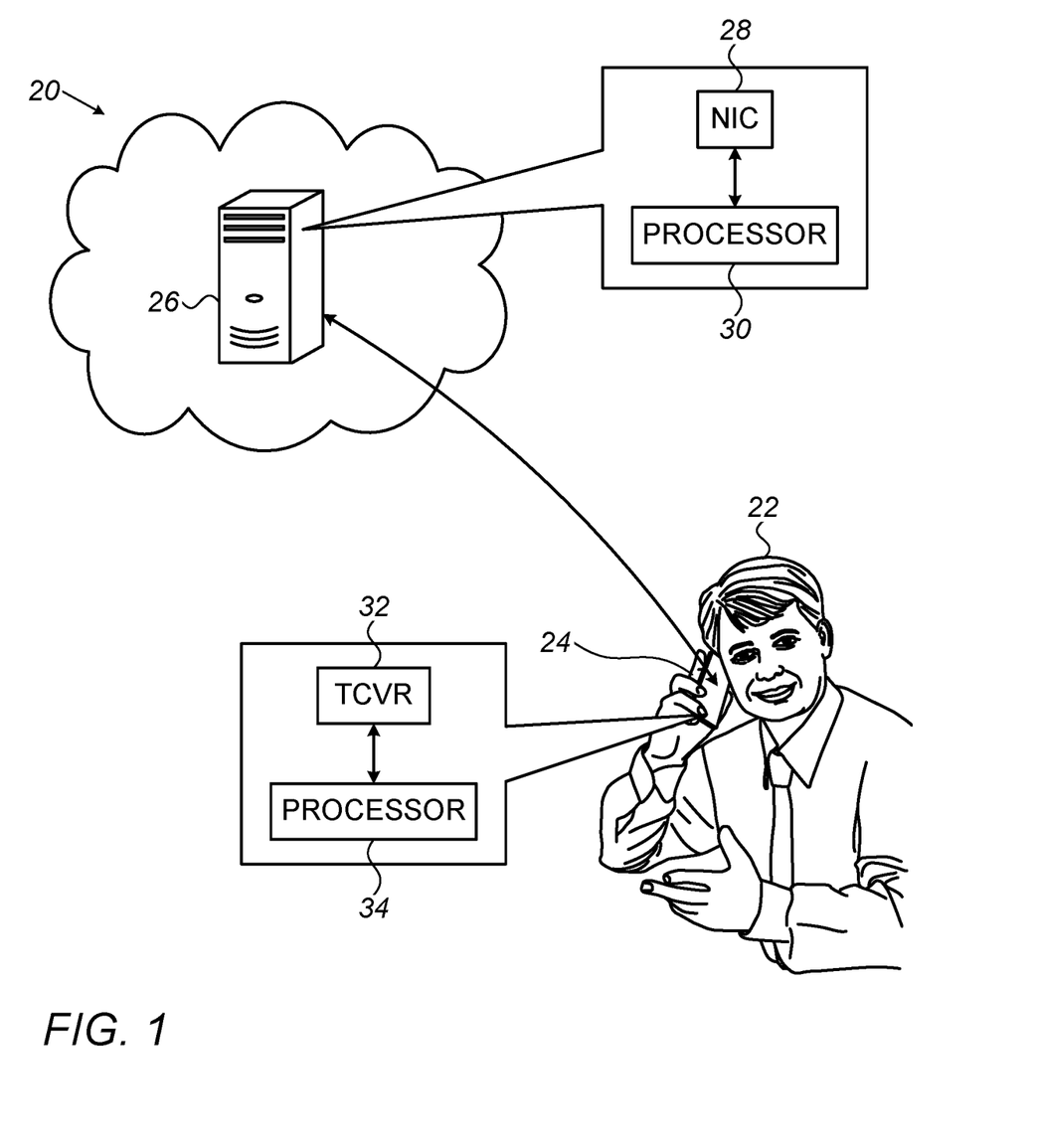
FIG. 1 is a schematic illustration of a system for assessing the status of a pulmonary condition, in accordance with some embodiments of the present invention.

Reference is initially made to FIG. 1, which is a schematic illustration of a system 20 for assessing the status of a pulmonary condition, in accordance with some embodiments of the present invention. System 20 comprises a device for communication and/or computing, such as a smartphone 24 or other mobile communication terminal, and a server 26. A subject 22, who suffers from a pulmonary condition such as pulmonary edema or pleural effusion, speaks into smartphone 24, typically during the course of the subject's normal day-to-day conversational activities. The smartphone transmits the subject's speech to server 26, which then analyzes the speech, as further described below, such as to assess the status of the pulmonary condition. (Such an analysis may be performed offline, or in real-time, as the subject is speaking.) The server then returns the results of the analysis to the smartphone, which then generates an output, such as an audio and/or visual output, indicative of the status of the pulmonary condition. For example, in response to the server identifying a deterioration in the status, the server may, via the smartphone, provide an alert indicative of the deterioration, and/or instruct the subject to speak with his physician, take his prescribed medication, and/or adjust the type of, or increase the dosage of, the medication taken. Conversely, in response to an improvement in, or stabilization of, the subject's status, the system may recommend a decrease in a medication dosage.

In some embodiments, the server is configured to communicate outputs, such as the results of an analysis and/or an alert, to a remote terminal, alternatively or additionally to communicating these outputs to the subject's smartphone. Thus, for example, the server may communicate outputs to the subject's physician, caregiver, insurance company, or employer, or to a hospital, an emergency call center, or a data center. Alternatively or additionally, the smartphone may communicate outputs to such remote terminals.

In some embodiments, the smartphone is configured to control a medicine pump. In such embodiments, in response to a deterioration in the subject's condition, the smartphone may automatically increase a dosage of medication delivered to the subject by the pump, without necessarily generating an alert. Subsequently, a follow-up analysis may be performed, to ascertain if the increase in dosage was successful. If the increase in dosage was not successful, an alert may be generated. Alternatively or additionally, the smartphone may be configured to control a diuretic pump in response to the results of an analysis; for example, the smartphone may automatically change the operating frequency of the pump.

In general, the response to a deterioration typically depends on the magnitude of the deterioration. For example, for a relatively small deterioration, the system may recommend, or automatically implement, an increase in the frequency at which the subject's speech is analyzed, and/or expand the analysis to identify additional parameters that may be relevant to the subject's condition, without necessarily generating an alert. For a larger deterioration, an alert may be generated, and/or the system may recommend, or automatically implement, an increased dosage of medication, such as a diuretic. Alternatively or additionally, the system may recommend that the subject see a doctor. In yet more extreme cases, the system may automatically contact an emergency call center.

Typically, server 26 is remote from subject 22, residing, for example, "in the cloud." The server comprises a network interface, such as a network interface controller (NIC) 28, which receives input from, and transmits output to, the smartphone. The server further comprises a processor 30, which, based on inputs received from the smartphone via NIC 28, computes relevant outputs, and returns these outputs, via NIC 28, to the smartphone. Analogously, the smartphone comprises a processor 34, and a network interface, such as a wireless transceiver (TCVR) 32, which is used by processor 34 to exchange communication with the server. The smartphone further comprises an acoustic sensor, configured to receive sounds that are emitted by the subject.

In alternative embodiments, a local processor, such as processor 34, or the processor of another local computing device, such as a laptop or desktop computer, processes the speech of the subject. For example, the subject may speak into a microphone belonging to a laptop computer, and the processor of the laptop computer may then process the resulting speech signals from the microphone.

Typically, processor 34 performs the relevant functions described herein by executing program instructions provided by a dedicated software application. The software application is typically run continuously, by the processor, in the background, such that the subject may continue regular usage of the smartphone while the application is running. Upon the subject beginning to speak into the phone, the application—without the subject necessarily noticing—begins to record, and/or transmit, the subject's speech. Alternatively, the application may be manually activated by the subject, and/or may be automatically activated by the processor, upon the subject initiating or answering a call.

Typically, the application instructs processor 34 to send a speech signal to the server for analysis, whenever a particular duration has passed from the most recent analysis, or whenever the server or the subject requests an analysis. Processor 34 may then wait for the subject to engage in a phone call, at which point, following receipt of a speech signal, the processor may send the speech signal to the server. Alternatively, the processor may prompt the subject (e.g., by displaying a message on the smartphone display) to speak into the smartphone, such that a speech signal may be obtained. In some embodiments, the server automatically places a call to the subject (by automatically calling the smartphone), and then, upon the subject answering the call, prompts the subject to speak. For example, the server may ask a question to the subject, such as "Did you take your medicine today?" (The question may be recorded or voice-synthesized.) Upon receiving the subject's answer, the server may analyze the answer for meaning and/or vocal properties, as described below.

Alternatively, the subject may be prompted to speak in any other suitable way, such as by receiving instructions to do so from medical personnel. In some embodiments, the subject may be prompted, e.g., by the smartphone, to perform a particular action prior to speaking, such as taking a certain number of steps, or climbing a certain number of stairs.

Typically, as noted above, processor 30 analyzes natural, "free" speech of the subject. In some cases, however, the subject may be prompted, e.g., by processor 34, to recite particular words or sentences that have been found to facilitate the analysis described herein, and these words or sentences may then be communicated to the server for analysis. (The same particular words or sentences may be used each time the analysis is performed, in order to facilitate a more effective assessment of the subject's condition.)

In some embodiments, the meaning (i.e., semantic content) of the subject's speech is automatically identified, and the assessment of the status of the condition is performed in response to the meaning. For example, the subject may be prompted, e.g., by the smartphone, to provide the speech by orally responding to a particular question. The subject's oral response to the question is then be analyzed both for the identification of the speech-related parameters described herein—which describe the vocal properties, such as spectral and/or cepstral properties, of the response—and for the meaning of the response. (The question may be posed visually, on the display of the smartphone, and/or auditorily.) Examples of such questions include "Did you take your medicine today?," "How do you feel?," and "How active were you today?" By identifying both the vocal properties of, and meaning of, the subject's answer, the status of the subject's condition may be better assessed. (In such embodiments, the subject may be required to select an answer from a predetermined group of candidate answers, to facilitate the analysis.) For example, if the subject responds "Yes" to the question "Did you take your medicine today?," but the speech-related parameters indicate a deterioration in the subject's condition, the processor may ascertain that the dosage of medicine prescribed to the subject is not high enough.

In some cases, processor 30 may analyze particular, possibly meaningless, sounds, such as a prolonged "ahh." (Processor 34 of the smartphone may be configured to prompt the subject to utter such sounds, upon receiving a request from the server to do so.) In analyzing these sounds, processor 30 may identify any one or more of the relevant parameters described herein. These parameters may then be used, optionally in combination with one or more other parameters derived from natural speech of the subject, to assess the status of the subject's condition.

In general, processor 30 may analyze the subject's speech at any suitable predetermined times, separated by any suitable intervals. For example, the processor may analyze the subject's speech immediately after hospitalization (when the subject's condition is relatively stable), one week after hospitalization, and three weeks after hospitalization. Alternatively, for example, the processor may analyze the subject's speech daily (beginning, for example, upon the subject's release from the hospital), or every other day. In some embodiments, the analysis schedule is customized to the subject's perception of the subject's condition; for example, an analysis may be performed upon the subject perceiving an improvement or deterioration in the subject's condition.

In general, each of processor 30 and processor 34 may be embodied as a single processor, or as a cooperatively networked or clustered set of processors. Each of processor 30 and processor 34 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data, are loaded into the RAM for execution and processing by the CPU and results are generated for display, output, transmittal, or storage, as is known in the art. The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2:
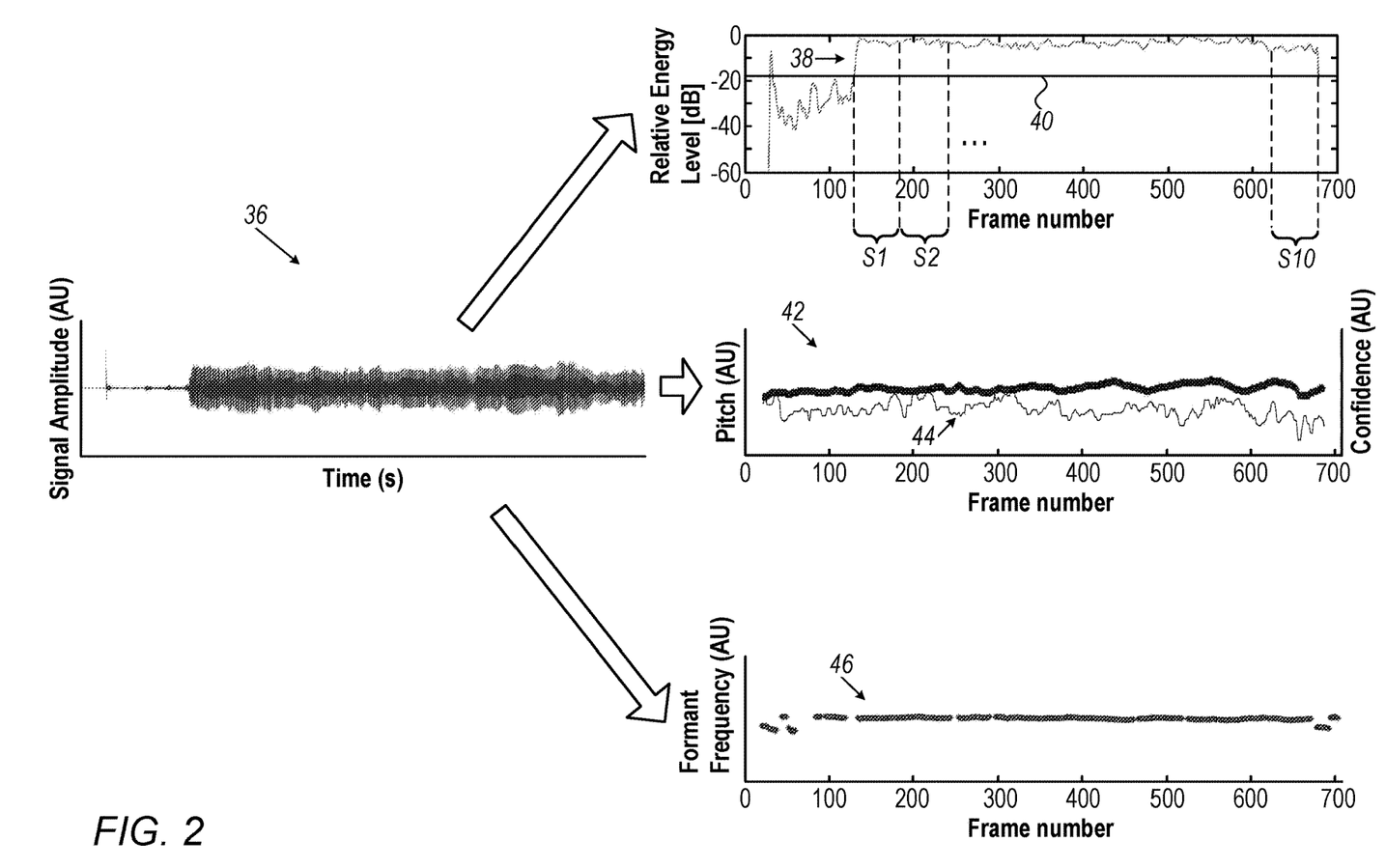
FIG. 2 is a schematic illustration of a preprocessing method performed by a processor, in accordance with some embodiments of the present invention.

Reference is now made to FIG. 2, which is a schematic illustration of a preprocessing method performed by processor 30, in accordance with some embodiments of the present invention.

In some embodiments, prior to analyzing the speech signal received from the smartphone, processor 30 preprocesses the speech signal, in order to identify those portions of the signal that are most suitable for analysis. FIG. 2 shows, on the left, the original speech signal 36, in the time domain, received from the smartphone. Typically, the processor first separates signal 36 into a plurality of (possibly overlapping) frames, each of which includes several samples. (For example, assuming a sampling rate of 8 kHz, a frame of 40 ms would include 320 samples.) Then, from signal 36, the processor derives one or more metrics, which are used by the processor to select those portions of the signal that are most suitable for analysis.

For example, the processor may compute the energy level 38 of the speech signal, expressed, for example, on a logarithmic scale relative to the maximum energy level in the signal. The processor may then select, for analysis, the largest contiguous portion of the signal whose energy level is above a particular threshold 40. Alternatively or additionally, the processor may compute the pitch 42 of the speech signal, and a corresponding confidence level 44, which indicates the confidence with which the pitch calculation was performed. The processor may then select portions of the signal for analysis, based on the pitch values, and/or the pitch confidence levels. For example, the processor may select the largest contiguous portion of the signal in which the stability of the pitch is above a particular threshold, i.e., the pitch changes by less than a particular threshold, and/or the confidence of the pitch calculation is above a particular threshold. Alternatively or additionally, the processor may calculate at least one formant frequency 46 of each frame belonging to the signal, and base the selection on the stability of the formant frequency.

Typically, all of the above-described selection criteria are implemented. That is, typically, the processor selects only those portions of the signal whose (i) energy level is above the threshold, (ii) pitch is sufficiently stable, (iii) pitch confidence is sufficiently high, and (iv) formant frequency is sufficiently stable. In particular, following the selection of a portion of a signal based on the energy-level criterion, the processor typically divides the signal into a plurality of larger segments, each segment including several frames, and then selects, for analysis, a consecutive sequence of segments that satisfy the pitch-based and formant-based selection criteria described above. For example, assuming that frames 131 through 680 have sufficient energy (as roughly indicated by FIG. 3), the processor may divide frames 131 through 680 into ten segments S1, S2, . . . S10, each segment including 55 frames. Then, a consecutive subset of these segments (e.g., the second through ninth of these segments) may be selected, based on the pitch-based and formant-based selection criteria.

It is emphasized that the above-described preprocessing typically does not involve cleaning the speech signal in any way. In other words, processor 30 typically does not alter the speech signal, in order to render the signal more suitable for analysis. Rather, as described above, the processor selects any suitable portions of the signal, while preserving the original content of these portions. If an insufficiently-large portion of the signal is found to be suitable for analysis, processor 30 may instruct the smartphone to transmit another signal to the server. Following the above-described preprocessing technique, processor 30 analyzes the portion of the speech signal that was ascertained to be suitable for analysis, such as to identify one or more speech-related parameters of the speech. Then, in response to the parameters, the processor assesses the status of the pulmonary condition. For example, the processor may identify at least one formant frequency of the speech (e.g., the formant frequency F1, F2, F3, and/or F4), and assesses the status of the pulmonary condition in response to the formant frequency. Typically, the processor assesses the status of the pulmonary condition by comparing the formant frequency to a baseline (or "reference") frequency. Such a baseline frequency may be a formant frequency, of the subject's speech, that was measured at an earlier date. If the current formant frequency is greater than this baseline, the subject's condition has deteriorated; conversely, if the current formant frequency is less than this baseline, the subject's condition has improved. If the current formant frequency is approximately equal to the baseline, the subject's condition is stable.

For example, the processor may use, as the baseline, a formant frequency that was measured (e.g., by the processor, using techniques described herein) upon the subject's release from hospital. If the current formant frequency is greater than this baseline, the subject's condition has deteriorated; on the other hand, little change in the formant frequency may indicate that the subject's condition remains stable.

Alternatively, such a baseline frequency may be a target (or "plateau") frequency at which the subject's condition is deemed to be stable, or a "borderline" frequency at which intervention and/or hospitalization is required. (Such baselines may be established separately for each subject, based on the subject's medical history.) The processor may assess the current status of the pulmonary condition, by comparing the current formant frequency to such a baseline. In some embodiments, an alert is generated if the difference between the current formant frequency and the target frequency is greater than a particular threshold, or if the current formant frequency is greater than the borderline frequency.

In some embodiments, the subject's formant frequency is measured over a period of time during which the subject is deemed (e.g., by a physician) to be healthy. The mean of these measurements is then taken as the baseline, and the standard deviation of these measurements is used to define a threshold at which alerts are generated. For example, an alert may be generated if a subsequent formant frequency exceeds the baseline by more than two standard deviations. As a purely illustrative example, the formant frequency F1 may have a baseline of 230 Hz with a standard deviation of 17 Hz, such that an alert is generated if F1 exceeds 264 Hz.

In some cases, such as where the subject's history is not available, the baseline may be based on population averages. In this regard, relevant characteristics of the subject—such as the subject's gender, weight, height, age, or level of physical activity—may be obtained, and used to choose a suitable baseline. For example, a population of individuals may be clustered into a plurality of clusters, based on relevant characteristics of the individuals, and a baseline for the subject may then be selected, by computing the average of the relevant parameter (e.g., the formant frequency) for the cluster in which the subject falls.

In some embodiments, the processor identifies a trend in the formant frequency, and generates an output, such as an alert, based on the identified trend. For example, if the processor identifies an increase in the formant frequency over a certain number of days, the processor may identify a deterioration in the subject's condition, and hence, generate an alert. (Such an alert may be generated even if the formant frequency has not exceeded the threshold that is based on the baseline frequency.) Alternatively, if the processor identifies a decrease in the formant frequency over a certain number of days, the processor may generate an output that indicates an improvement in the subject's condition.

In some embodiments, to identify the formant frequency, the processor first identifies the respective formant frequency of each of the frames in the selected segments. (The processor may first apply a Hamming window to each of the frames, and/or filter each frame with a pre-emphasis filter.) Next, the formant frequency of the speech (i.e., the speech signal as a whole) is identified, based on the respective formant frequencies of the frames. For example, the processor may compute the mean, or median, of the respective formant frequencies of the frames, and identify this metric as the formant frequency of the speech.

Figure 3:
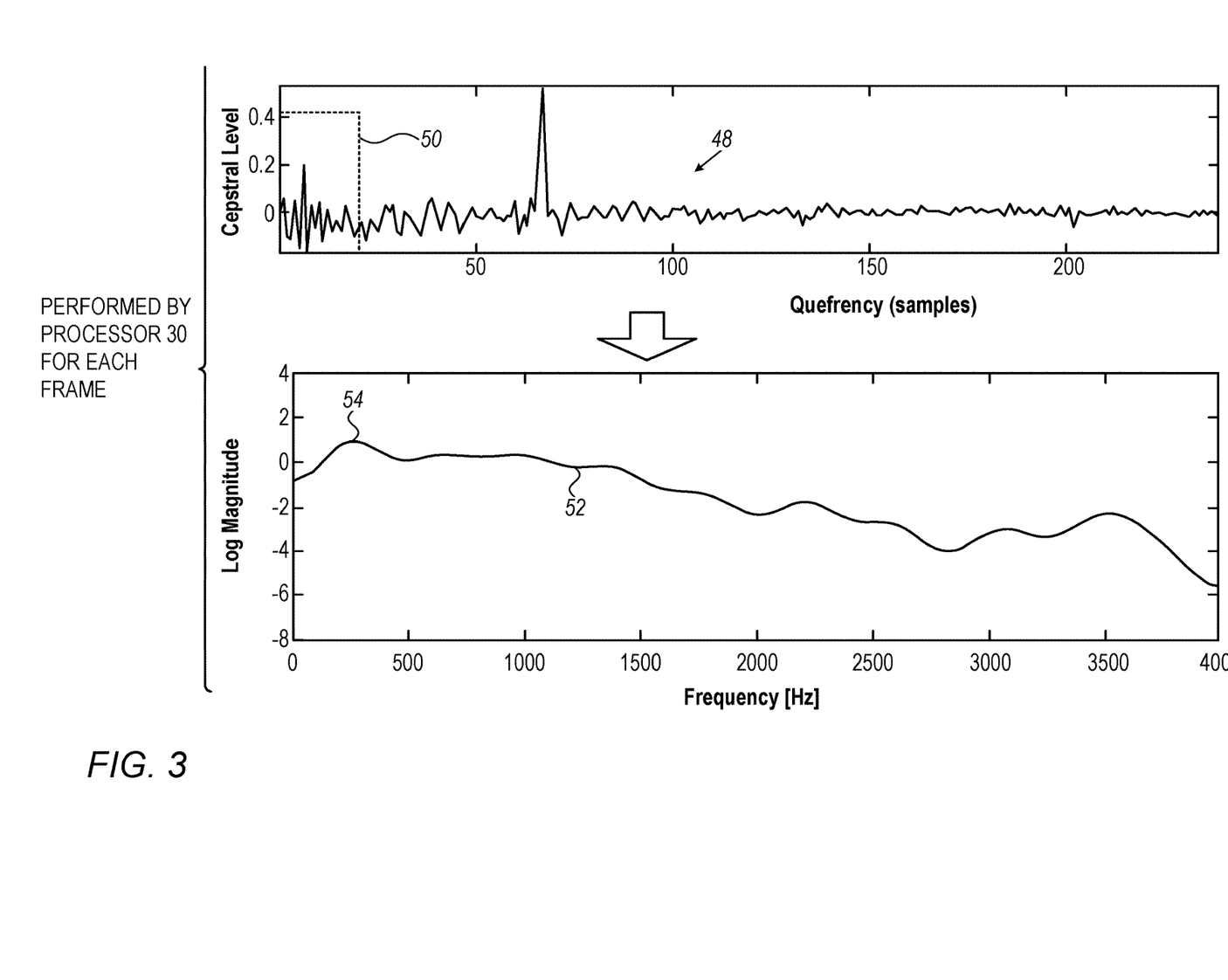
FIG. 3 is a schematic illustration of a method for analyzing speech of a subject, in accordance with some embodiments of the present invention.

Reference is now made to FIG. 3, which is a schematic illustration of a method for analyzing speech of a subject, in accordance with some embodiments of the present invention. The method illustrated in FIG. 3 facilitates the identification of a formant frequency.

Per this method, which is performed in some embodiments, the processor first computes a cepstrum 48 of each frame, which is the inverse Fourier transform of the logarithm of the magnitude of the Fourier transform of the frame, following phase unwrapping. Cepstrum 48 has both a real and imaginary component. In some embodiments, both of these components are analyzed by the processor, while in other embodiments, the processor analyzes only the real component. The latter is assumed for FIG. 3 and the description below; that is, it is assumed that the "cepstral level" plotted in FIG. 3 is the real component of the cepstrum, and that the processing described below is performed on this real component. (The independent variable of a cepstral graph is called the "quefrency," which is measured in units of samples.)

Subsequently, the processor applies a low-pass cepstral lifter 50 to the cepstrum of the frame. (A filter operating on a cepstrum is referred to as a "cepstral lifter.") A suitable cutoff quefrency for cepstral lifter 50 may be found by requiring that the inverse-transformed liftered cepstrum have a threshold level of smoothness, indicating sufficient liftering-out of the periodic portion of the cepstrum.

Subsequently, the processor inverse-transforms the liftered cepstrum to the frequency domain, such as to derive an inverse-transformed liftered cepstrum signal 52. Then, the processor identifies a formant frequency of the frame, by identifying a peak 54 of signal 52. For example, assuming that peak 54 is located at 350 Hz, the formant frequency of the frame would be 350 Hz. (In the example shown in FIG. 3, the identified formant frequency is the F1 formant. In other cases, the processor may identify other formant frequencies, such as F2, alternatively or additionally to F1.)

As described above, the processor performs the above-described technique for each of the frames of signal 36, and then calculates a single, overall formant frequency from the frame-specific formant frequencies. This overall formant frequency is then used to assess the status of the subject's condition.

Alternatively or additionally, the processor may assess the status of the subject's condition in response to other speech-related parameters extracted from signal 36. Such other parameters may include: a set of mel-frequency cepstrum coefficients (MFCCs) or derivatives thereof, a set of relative spectral transform-perceptual linear prediction (RASTA-PLP) cepstrum components, and/or a set of RASTA-PLP spectrum components. Various other parameters that may be identified from the speech of the subject, and used to assess the subject's condition, include a period of time between breaths, a number of pauses in the speech, loudness of the speech, vocal irregularities, a number of stutters, and an exhalation length, as well as any relevant frequency or pitch parameters. As an example of the latter, the subject's condition may be assessed based on the subject's inability to produce low frequencies, or based on observed changes in distortion.

Alternatively or additionally, the processor may base the assessment on other, non-speech-related parameters, such as a picture of the subject (which may be acquired, for example, while the subject is speaking, by a camera belonging to the smartphone, or by an external camera), the subject's weight, an echocardiogram (ECG) recording taken from the subject, the subject's arterial oxygen saturation, and/or the subject's level of activity (quantified, for example, as a number of steps taken during a preceding period of time). Any of these parameters may be input to the smartphone, e.g., by the subject. In some embodiments, the smartphone is functionally linked, e.g., wirelessly, to an external device that is configured to measure one or more of these or any other parameters, such as, for example, a camera, a spirometer, a pulse oximeter, an electrocardiograph, a heart rate monitor, a blood pressure monitor, a skin-conductivity sensor, or a posture monitor.

In some embodiments, the processor applies a machine-learned model, such as a classifier or regressor, to some or all of the aforementioned parameters. In such embodiments, the processor is typically also configured to learn the model, based on a plurality of labeled speech recordings. For example, the processor may be provided with a plurality of speech recordings, each labeled as either "wet," indicating that the recording was obtained immediately before dialysis treatment, or "dry," indicating that the recording was obtained immediately after dialysis treatment. Each of these recordings may then be preprocessed, as described above, such as to select the most suitable portion of each recording for parameter (or "feature") extraction. Relevant parameters are then extracted from each recording, and fed to a machine-learning algorithm, such as K Nearest Neighbors (KNN), Decision Trees, or Support Vector Machines (SVM), e.g., with a Gaussian kernel. For example, in some embodiments, the processor extracts, from each frame of each selected portion of each recording, a set of 60 parameters, including (i) a set of 12 MFCCs, (ii) a set of 12 MFCC first derivatives, (iii) a set of 12 MFCC second derivatives, (iv) a set of 8 RASTA-PLP cepstrum components, and (v) a set of 8 RASTA-PLP spectrum components. Typically, a dimensionality reduction algorithm, such as Principal Component Analysis (PCA), is then used reduce the dimensionality of the full set, e.g., to 48 dimensions. This reduced set of parameters is then fed, along with the associated labels, to the relevant machine-learning algorithm. The algorithm then learns a model, which may be applied to subsequent recordings. For example, the algorithm may learn to classify subsequent recordings as either "wet" or "dry."

(In general, assuming D dimensions, F frames per recording, and N recordings, the "training set" fed to the algorithm includes a matrix of size D×FN. For example, assuming 20 recordings (e.g., 10 "wet" recordings and 10 "dry" recordings), 150 frames per recording, and 48 dimensions, the training set includes a matrix of size 48×3000.)

In some embodiments, to classify a subsequent recording, the processor first classifies, separately, each frame of the recording. (As described above, the processor may use only the frames belonging to the most suitable portion of the recording.) For example, the processor may apply a learned SVM model, which returns, for each frame, a probability between 0 and 1, with 0 indicating "dry," and 1 indicating "wet." In applying such a model, the processor may set suitable decision thresholds, such that, for example, probabilities below 0.3 deliver a "dry" decision, probabilities above 0.7 deliver a "wet" decision, and intermediate probabilities do not deliver a decision at all. The processor may then compare the total number of "dry" decisions to the total number of "wet" decisions, and apply to the recording the classification that received the greater number of decisions. (In performing this comparison, the processor may give a higher weighting to a probability that is closer to 0 or 1, relative to a probability that is closer to the decision threshold.)

Typically, a separate model is learned for each subject, by acquiring training data from the subject over a suitable period of time, and then applying a suitable machine-learning algorithm to these data.

Although the present disclosure relates mainly to pulmonary conditions associated with the accumulation of excess fluid inside or near the lungs, it is noted that the embodiments described herein may also be applied to other types of pulmonary conditions, such as chronic obstructive pulmonary disease (COPD) or asthma, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
a network interface; and
a processor, configured:
to receive, via the network interface, a signal representing speech of a subject who suffers from a pulmonary condition related to accumulation of excess fluid,
to identify, by performing a spectral analysis of the signal, one or more spectral properties of the speech,
to assess, in response to the properties, a status of the pulmonary condition by identifying a change in an amount of the fluid present in an anatomical portion of the subject selected from the group of anatomical portions consisting of: parenchyma of lungs of the subject, and a pleural cavity of the subject, and
to generate, in response thereto, an output indicative of the status of the pulmonary condition.

2. The apparatus according to claim 1, wherein the processor is configured to perform the spectral analysis by performing a cepstral analysis of the signal.

3. The apparatus according to claim 1, wherein the processor is further configured to identify, by analyzing the speech, a meaning of the speech, and wherein the processor is configured to assess the status in response to the meaning.

4. The apparatus according to claim 1, wherein the processor is further configured to prompt the subject to provide, by orally responding to a question, the speech.

5. The apparatus according to claim 4, wherein the processor is configured to prompt the subject to provide the speech by:
placing a call to the subject, and
upon the subject answering the call, asking the question to the subject.

6. The apparatus according to claim 1, wherein the condition is selected from the group consisting of: pulmonary edema, and pleural effusion.

7. The apparatus according to claim 1, wherein the processor is configured to generate the output by providing an alert indicative of a deterioration in the status.

8. The apparatus according to claim 1, wherein the properties include at least one formant frequency of the speech.

9. The apparatus according to claim 8, wherein the processor is configured to assess the status of the pulmonary condition by comparing the formant frequency to a baseline frequency.

10. The apparatus according to claim 8, wherein the processor is configured to identify the formant frequency by:
for each frame of the signal:
computing a cepstrum of the frame,
subsequently, applying a low-pass cepstral lifter to the cepstrum of the frame,
subsequently, inverse-transforming the liftered cepstrum to a frequency domain, and
subsequently, identifying a frame-specific formant frequency of the frame, by identifying a peak of the inverse-transformed liftered cepstrum, and
identifying the formant frequency, based on the respective frame-specific formant frequencies of the frames.

11. The apparatus according to claim 1, wherein the processor is configured to perform the spectral analysis by:
selecting at least one portion of the signal for analysis, based on one or more metrics selected from the group consisting of: an energy level of the speech, a stability of a pitch of the speech, a confidence in a calculation of the pitch of the speech, and a stability of a formant frequency of the speech, and
subsequently, performing the spectral analysis on the selected portion of the signal.

12. The apparatus according to claim 1, wherein the processor is configured to assess the status of the pulmonary condition by applying a machine-learned model to the properties.

13. The apparatus according to claim 1, wherein the properties include a set of mel-frequency cepstrum coefficients (MFCCs).

14. The apparatus according to claim 1, wherein the properties include a set of derivatives of mel-frequency cepstrum coefficients (MFCCs).

15. The apparatus according to claim 1, wherein the properties include a set of relative spectral transform-perceptual linear prediction (RASTA-PLP) cepstrum components.

16. The apparatus according to claim 1, wherein the properties include a set of relative spectral transform-perceptual linear prediction (RASTA-PLP) spectrum components.

17. The apparatus according to claim 1, wherein the processor is configured to assess the status of the pulmonary condition without identifying any cough sounds, and without identifying any wheezing sounds, in the signal.

18. The apparatus according to claim 1, wherein the processor is configured to receive the signal without first prompting the subject to provide the speech.

19. A method, comprising:
using a processor, by performing a spectral analysis of a signal representing speech of a subject who suffers from a pulmonary condition related to accumulation of excess fluid, identifying one or more spectral properties of the speech;
in response to the properties, automatically assessing a status of the pulmonary condition by identifying a change in an amount of the fluid present in an anatomical portion of the subject selected from the group of anatomical portions consisting of: parenchyma of lungs of the subject, and a pleural cavity of the subject; and
in response thereto, generating an output indicative of the status of the pulmonary condition.

20. The method according to claim 19, wherein performing the spectral analysis comprises performing the spectral analysis by performing a cepstral analysis of the signal.

21. The method according to claim 19, further comprising, by automatically analyzing the speech of the subject, identifying a meaning of the speech, wherein assessing the status comprises assessing the status in response to the meaning.

22. The method according to claim 19, further comprising prompting the subject to provide, by orally responding to a question, the speech.

23. The method according to claim 22, wherein prompting the subject to provide the speech comprises:
   automatically placing a call to the subject, and
   upon the subject answering the call, using the processor, asking the question to the subject.

24. The method according to claim 19, wherein the condition is selected from the group consisting of: pulmonary edema, and pleural effusion.

25. The method according to claim 19, wherein generating the output comprising providing an alert indicative of a deterioration in the status.

26. The method according to claim 19, wherein the properties include at least one formant frequency of the speech.

27. The method according to claim 26, wherein assessing the status of the pulmonary condition comprises assessing the status of the pulmonary condition by comparing the formant frequency to a baseline frequency.

28. The method according to claim 26, wherein identifying the formant frequency comprises:
   for each frame of the signal:
      computing a cepstrum of the frame,
      subsequently, applying a low-pass cepstral lifter to the cepstrum of the frame,
      subsequently, inverse-transforming the liftered cepstrum to a frequency domain, and
      subsequently, identifying a frame-specific formant frequency of the frame, by identifying a peak of the inverse-transformed liftered cepstrum; and
   identifying the formant frequency, based on the respective frame-specific formant frequencies of the frames.

29. The method according to claim 19, wherein performing the spectral analysis comprises:
   selecting at least one portion of the signal for analysis, based on one or more metrics selected from the group consisting of: an energy level of the speech, a stability of a pitch of the speech, a confidence in a calculation of the pitch of the speech, and a stability of a formant frequency of the speech, and
   subsequently, performing the spectral analysis on the selected portion of the signal.

30. The method according to claim 19, wherein assessing the status of the pulmonary condition comprises assessing the status of the pulmonary condition by applying a machine-learned model to the properties.

31. The method according to claim 19, wherein the properties include a set of mel-frequency cepstrum coefficients (MFCCs).

32. The method according to claim 19, wherein the properties include a set of derivatives of mel-frequency cepstrum coefficients (MFCCs).

33. The method according to claim 19, wherein the properties include a set of relative spectral transform-perceptual linear prediction (RASTA-PLP) cepstrum components.

34. The method according to claim 19, wherein the properties include a set of relative spectral transform-perceptual linear prediction (RASTA-PLP) spectrum components.

35. The method according to claim 19, wherein assessing the status of the pulmonary condition comprises assessing the status of the pulmonary condition without identifying any cough sounds, and without identifying any wheezing sounds, in the signal.

36. The method according to claim 19, further comprising receiving the signal without first prompting the subject to provide the speech.

37. A system, comprising:
   a mobile communication terminal; and
   a server, comprising a processor configured:
      to receive, from the mobile communication terminal, a signal representing speech of a subject who suffers from a pulmonary condition related to accumulation of excess fluid,
      to identify, by performing a spectral analysis of the signal, one or more spectral properties of the speech,
      to assess, in response to the properties, a status of the pulmonary condition by identifying a change in an amount of the fluid present in an anatomical portion of the subject selected from the group of anatomical portions consisting of: parenchyma of lungs of the subject, and a pleural cavity of the subject, and
      to generate, in response thereto, an output indicative of the status of the pulmonary condition.

38. A computer software product comprising a tangible non-transitory computer-readable medium in which program instructions are stored, which instructions, when read by a processor, cause the processor:
   to receive a signal representing speech of a subject who suffers from a pulmonary condition related to accumulation of excess fluid,
   to identify, by performing a spectral analysis of the signal, one or more spectral properties of the speech,
   to assess, in response to the properties, a status of the pulmonary condition by identifying a change in an amount of the fluid present in an anatomical portion of the subject selected from the group of anatomical portions consisting of: parenchyma of lungs of the subject, and a pleural cavity of the subject, and
   to generate, in response thereto, an output indicative of the status of the pulmonary condition.

39. Apparatus, comprising:
   an acoustic sensor; and
   a processor, configured:
      to receive, via the acoustic sensor, a signal representing speech of a subject who suffers from a pulmonary condition related to accumulation of excess fluid,
      to identify, by performing a spectral analysis of the signal, one or more spectral properties of the speech,
      to assess, in response to the properties, a status of the pulmonary condition by identifying a change in an amount of the fluid present in an anatomical portion of the subject selected from the group of anatomical portions consisting of: parenchyma of lungs of the subject, and a pleural cavity of the subject, and
      to generate, in response thereto, an output indicative of the status of the pulmonary condition.

* * * * *